Figure 1:
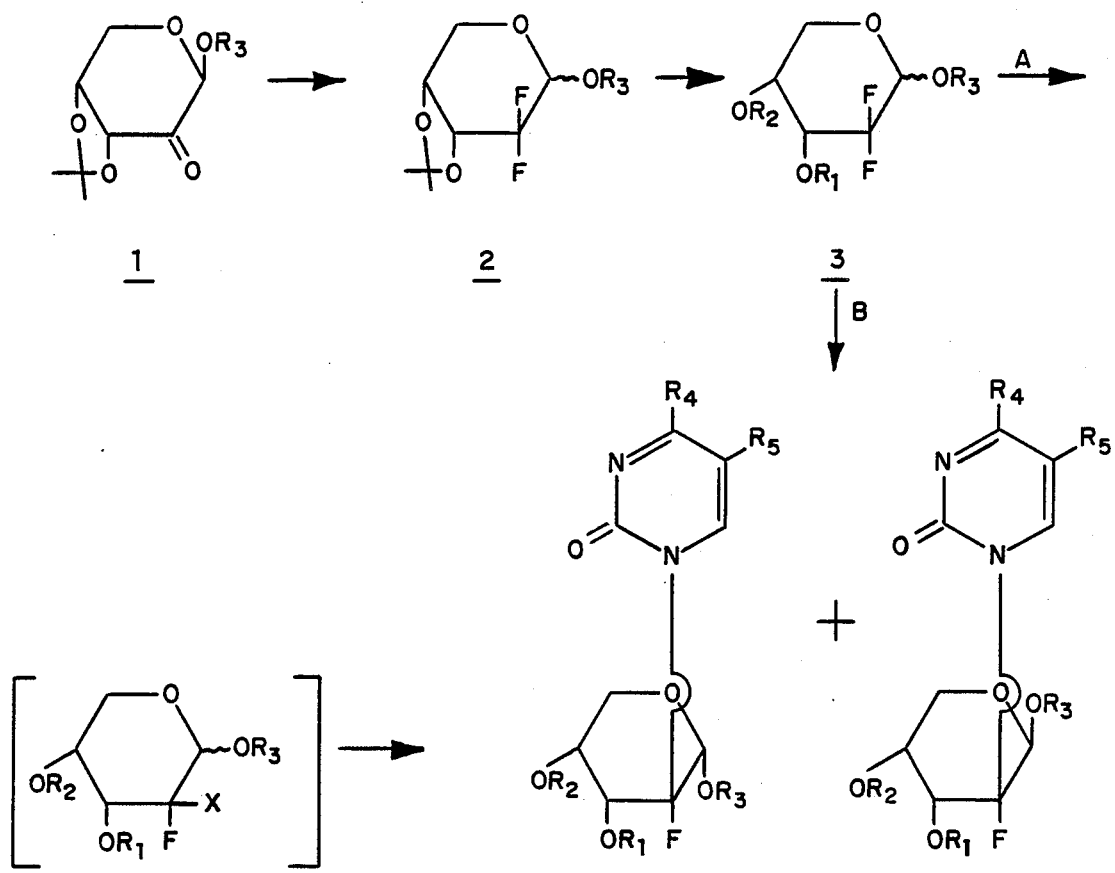

United States Patent [19]

Bobek et al.

[11] Patent Number: 4,918,056

[45] Date of Patent: Apr. 17, 1990

[54] 2-SUBSTITUTED ARABINOPYRANOSYL NUCLEOSIDES AND NUCLEOTIDES

[75] Inventors: Miroslav V. Bobek; Seung-Ho An, both of Williamsville; Ralph J. Bernacki, Elma, all of N.Y.

[73] Assignee: Health Research, Inc. (Roswell Park Division), Buffalo, N.Y.

[21] Appl. No.: 918,372

[22] Filed: Oct. 14, 1986

[51] Int. Cl.$^4$ .................... A61K 31/70; C07H 15/02
[52] U.S. Cl. ........................................ 514/25; 514/50; 536/4.1; 536/17.3; 536/18.1; 536/18.4; 536/23; 536/24; 536/120; 536/122
[58] Field of Search ................... 536/4.1, 17.3, 55; 514/25, 43

[56] References Cited

FOREIGN PATENT DOCUMENTS 1070413  6/1967  United Kingdom .

OTHER PUBLICATIONS

Ho et al, Chemical Abstracts, 105: 209314m (1986).
Kawaguchi et al, Chem. Pharm. Bull. 33(4) 1652–1659 (1985).
Narayanan et al, J. Org. Chem., 30 1734–1736 (1965).
Jung et al, J. Org. Chem. 42 (23) pp. 3761–3763 (1977).
Montgomery, Cancer Research 19(5), pp. 447–463 (1959).
Bobek et al, J. Med. Chem. 22 pp. 592–597 (1979).
British Publication–Tetrahed. Lett. 39: 3433–3436 (1977).
Kierzek, R. et al.: Tetrahed. Lett. 22: 3761 (1981).
E. Law et al., J. National Cancer Institute 10: 179–192, (1949).
National Cancer Institute (NCI) protocol 3LE31, described IN Vivo Cancer Models, NIH Publication 84–2635, Feb. 1984.
Cox, D. R. Journal Royal Stat, Soc, Series B 34: 187–220 (1972).
Dunn, O. J., Technometrics, 6: 241–252, 1964.
Bernacki et al.; Cancer Research 45: 695, 1985.
Bergstrom et al., Synthesis of Gem-Difluoro Substituted Nucleoside Analogs, Abstract from mtg of American Chemical Society, 1985.
Grindey et al., Antitumor Activity of 2',2'-difluorodeoxycytidine, Proceedings of AACR, vol. 27, Mar. 1986.
Kroin et al., A Practical Synthesis of 2'-deoxy-2'2'-difluoro-D-Ribofuranosyl Nucleosides, Abstract from mtg of American Chemical Society, 1986.
Hertel et al., A Simple and Stereocontrolled Synthesis of 2–Deoxy-2,2–Defluoro-D–Ribose, Abstract from mtg of American Chemical Society, 1986.

*Primary Examiner*—Johnnie R. Brown
*Assistant Examiner*—James O. Wilson
*Attorney, Agent, or Firm*—Anna E. Mack; Michael L. Dunn

[57] ABSTRACT

Novel arabinopyranosyl nucleoside derivatives having the heterocyclic moiety and fluorine at the 2' position of the sugar ring (pyranose configuration), which have antitumor, antiviral and antimicrobial properties, are prepared by condensation of a pyrimidine, purine or 1,3-oxazine base with an acylated 2-deoxy-2,2-difluoro-D-arabinopyranoside and/or acylated 2-deoxy-2-bromo-2-fluoro-D-arabinopyranoside.

7 Claims, 1 Drawing Sheet

2-SUBSTITUTED ARABINOPYRANOSYL NUCLEOSIDES AND NUCLEOTIDES

The invention described herein was made in the course of work under research grants CA13038 and CA24538 from the National Institutes of Health/National Cancer Institute.

BACKGROUND OF THE INVENTION

This invention relates to novel arabinopyranosyl nucleosides and nucleotides which exhibit useful antitumor, antiviral and antimicrobial activities, to methods of preparing these nucleosides and nucleotides, and to pharmaceutical compositions containing them. More particularly this invention relates to novel arabinopyranosyl nucleosides and nucleotides having the heterocyclic base and fluorine at the 2′-position of the sugar ring.

Several nucleic acid derivatives have been found to possess antitumor activity. Most of the agents developed to date, however, exhibit many undesirable toxic side effects or undergo rapid inactivation in vivo. Accordingly the need to develop new antineoplastic agents exhibiting improved therapeutic indices is still recognized throughout the pharmaceutical industry.

SUMMARY OF THE INVENTION

In accordance with the present invention there is provided a new class of arabinopyranosyl nucleoside and nucleotide derivatives possessing antitumor, antiviral and antimicrobial properties having the generic formula:

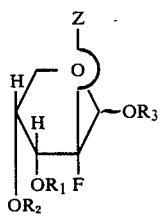

wherein Z is a pyrimidinyl-1, purinyl-9, or 1,3-oxazinyl-3 moiety, each of $R_1$ and $R_2$ is selected from the group consisting of hydrogen, isopropylidine, acetyl, propionyl, butyryl, valeryl, isovaleryl, hexanoyl, heptanoyl, octanoyl, nonanoyl, undecanoyl, lauroyl, benzoyl, phenylacetyl, phenylpropionyl, o-, m-, and p-methylbenzoyl, β-cyclopentylpropionyl, and dihydrocinnamoyl, and acid addition salts thereof, and $R_3$ is hydrogen, methyl, benzyl or an alkyl group.

Preparation of the 2′-fluoro nucleosides of the present invention may be accomplished by (a) blocking the labile hydrogen sites on the 3 and 4 positions of the sugar with acyl groups and (b) condensing the blocked sugar with pyrimidines, purines or 1,3-oxazines.

The pyrimidine, purine, or 1,3-oxazine base can be substituted or unsubstituted and may be acylated with hydrolyzable acyl groups.

A preferred group of pyrimidine bases are those corresponding to the formula

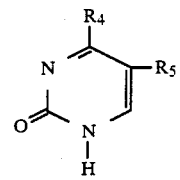

wherein $R_4$ is amino, hydroxy, thio, hydroxylamino, alkylamino, arylamino, or aralkylamino, and $R_5$ is fluoro, bromo, chloro, hydrogen, iodo, mercapto, nitro, nitrilo, thiocyanato, alkyl, alkenyl, or alkynyl.

A preferred group of purine bases are those corresponding to the formula

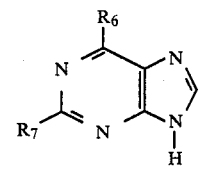

wherein $R_6$ is amino, hydrogen, hydroxylamino, thio, chloro, alkylamino, arylamino, or aralkylamino, and $R_7$ is hydrogen, oxo, chloro, fluoro, amino, nitro, thio, or hydroxyalkyl.

A preferred group of 1,3-oxazine bases are those corresponding to the formula

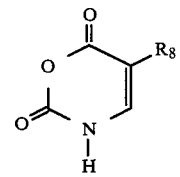

wherein $R_8$ is fluoro, bromo, chloro, hydrogen, iodo, mercapto, nitro, nitrilo, thiocyanate, alkyl, alkenyl, or alkynyl.

Suitable examples of pyrimidine bases include cytosine, uracil, thymine, 5-fluorouracil, 5-azauracil, 5-azacytosine, dihydro-5-azauracil, dihydro-5-azacytosine, 6-azauracil, 6-azacytosine, 3-deazauracil, and 3-deazacytosine. Examples of suitable purine bases include adenine, guanine, 6-chloropurine, hypoxanthine, and xanthine, as well as the 1-deaza, 2-aza, 3-deaza, 7-deaza, 8-aza, 2,8-diaza, 7-deaza-8-aza, and 9-deaza derivatives of those compounds.

Hydrolyzable acyl groups which may be present on the heterocyclic base include acetyl, propionyl, butyryl, valeryl, isovaleryl, hexanoyl, heptanoyl, octanoyl, nonanoyl, undecanoyl, lauroyl, benzoyl, phenylacetyl, phenylpropionyl, o-, m-, and p-methylbenzoyl, β-cyclopentylpropionyl, dihydrocinnamoyl, and the like.

Silylation or alkoxylation of the labile hydrogen sites on the heterocyclic base can be accomplished by known methods. Silylation, for example as described in British patent specification No. 1,070,413, can be used. The procedure generally involves reacting the labile hydrogen-containing base at about room temperature with a tri(lower) alky-chlorosilane in the presence of a tertiary amine in an anhydrous organic solvent such as benzene, toluene, xylene, and dioxane. Suitable tertiary amines include tri(lower) alkyl amines such as trimethylamine, triethylamine, and tripropylamine. Alternatively, silylation can be effected by suspending the base in anhydrous hexa(lower)alkyldisilazane and heating to reflux.

The nucleosides and nucleotides (basic compounds) of the present invention can be converted into the acid addition salts via reaction with acid, both organic and inorganic, such as aliphatic, alicyclic, araliphatic, aromatic and heterocyclic mono-and polybasic acids, sulfonic acids, and the well known mineral acids. Exemplary of suitable, physiologically acceptable salt forming acids are aliphatic, alicyclic, araliphatic, aromatic, heterocyclic, mono and polybasic carboxylic and sulfonic acids, exemplary of which are formic, acetic, propionic, pivalic, diethylacetic, oxalic, malonic, succinic, maleic, lactic, tartaric, malic, aminocarboxylic, sulfamic, benzoic, salicylic, phenylpropionic, citric, gluconic, ascorbic, nicotinic, isonicotinic methanesulfonic, p-toluene-sulfonic, sulfuric, nitric, hydrohalic, phosphoric acids and the like.

The compounds of this invention are useful as antineoplastic, antiviral and antibacterial agents, particularly anti-tumor agents. They are effective against five kinds of tumor cell growth including two drug resistant leukemias in mice and exhibit a significant improvement on therapeutic indices.

The compounds of the present invention can be prepared from starting reactants which are known or are commercially available. The synthesis of gem-difluorosaccharides was developed in 1977 and reported in the British publication, "Tetrahedron Letters", No. 39, 3433–3436 (1977). As reported therein useful procedures for fluorinating sugar aldehydes and ketones were exemplified by the following:

1. 6-Deoxy-6,6-difluoro-1,2:3,4-di-O-isopropylidene-α-D-galactopyranose having the formula

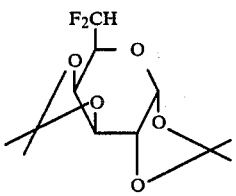

was prepared from crude 1,2:3,4-di-0-isopropylidene-α-D-galactohexodialdo-1,5-pyranose (8.16 g, 0.031 mol) which was dried by distilling 100 ml of dry toluene from its solution. It was then dissolved in 150 ml of $CH_2CL_2$ and 10 ml (0.08 mol) of diethylaminosulfur trifluoride (DAST) was added under $N_2$ to this solution. The reaction mixture was stirred at room temperature under nitrogen for 16 hours and was then washed with NaHCO$_3$ solution. The aqueous layer was extracted with $CH_2CL_2$ and the combined organic solution was dried ($Na_2SO_4$). The crude product, obtained by evaporating the solvent, was purified on a dry silica gel column using benzene as eluent.

The resulting compound was obtained as an oil (3.78 g, 46% yield) which solidified when kept at room temperature for a few days; m.p. 48°–50° C.

2. Methyl 2-deoxy-2,2-difluro-3,4-0-isopropylidene-α,β-L-erythro-pentopyranoside having the formula

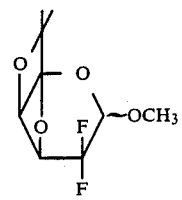

was prepared from methyl 3,4-O-isopropylidene-β-L-erythropentopyranosid-2-ulose (1.95 g, 0.0097 mol), which was prepared by the oxidation of methyl 3,4-O-isopropylidene-β-L-arabinopyranoside by DMSO-Ac$_2$O, and was dried by distilling approximately 100 ml of dry toluene from its solution. It was then dissolved in 100 ml of benzene and to this solution was added under $N_2$ 3 ml (0.024 mol) of DAST. The reaction mixture was refluxed for 16 hours under $N_2$, cooled, and then washed with NaHCO$_3$ solution. The aqueous layer was washed with CHCl$_3$ (50 ml) and the combined organic solution was dried ($Na_2SO_4$). Evaporation of this solution and purification of the residue on a dry silica gel column, using benzene as the eluent, gave 0.54 g (25% yield) of syrupy product.

These compounds were characterized by mass and $^{19}F$ nuclear magnetic resonance spectroscopy. In the mass spectra of these derivatives, $M^+ - 15$ peaks were obtained, resulting from the loss of one CH$_3$ group, which is a characteristic feature for sugar derivatives containing an isopropylidene group.

The synthesis of the arabinopyranosides described herein forms part of this invention and is carried out using a novel multiple step process comprising:

(a) oxidizing 3,4-O-isopropylidine-β-D-erythropentopyranoside through the use of CrO$_3$-2 pyridine reagents to obtain 3,4-O-isopropylidine-β-D erythro-pentopyranosid-2-ulose of the formula

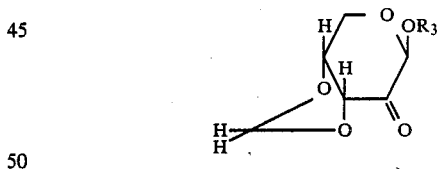

wherein $R_3$ is hydrogen, methyl, benzyl or an alkyl group, b) fluorinating the product of step (a) with diethylaminosulfur trifluoride (DAST) in benzene at room temperature in an amount sufficient to obtain an anomeric mixture of 2-deoxy-2,2-difluoro-3,4-O-isopropylidene-D-erythropentopyranosides of the formula

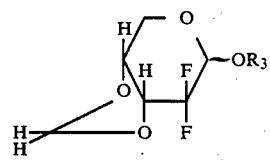

(c) hydrolyzing the product of step (b) with 95% formic acid to obtain free glycosides of the formula

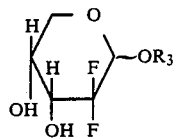

and (d) acylating the product of step (c) with acetic anhydride pyridine to obtain 3,4-di-O-acyl-2-deoxy-2,2-difluoro-D-erythropentopyranosides of the formula

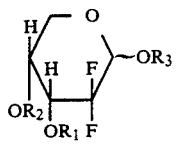

wherein each of $R_1$ and $R_2$ is selected from the group consisting of isopropylidene, acetyl, propionyl, butyryl, valeryl, isovaleryl, hexanoyl, heptanoyl, octanoyl, nonanoyl, undecanoyl, lauroyl, benzoyl, phenylacetyl, phenylpropionyl, o-, m-, and p-methylbenzoyl, β-cyclopentylpropionyl, and dihydrocinnamoyl, and acid addition salts thereof, and (e) halogenating the product of step (d) through the use of hydrogen bromide in methylene chloride to obtain the unstable 2-deoxy-2-bromo-2-fluoro-D-arabinopyranoside of the formula

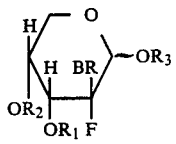

The sugar moiety, preferably selected from ribose, deoxyribose, lyxose and arabinose, and most preferably being ribose, deoxyribose or arabinose, is covalently bonded to the heterocyclic moiety at the 2'- position to form a nucleoside by a process comprising the further steps of (f) blocking the labile hydrogen sites on a pyrimidine, purine or 1,3-oxazine base by silylation or alkoxylation and (g) condensing the blocked base with the compound obtained in (e) above of the formula

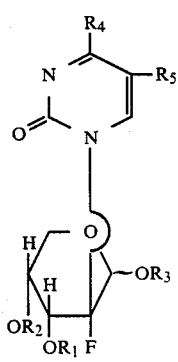

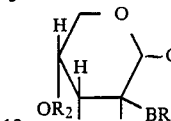

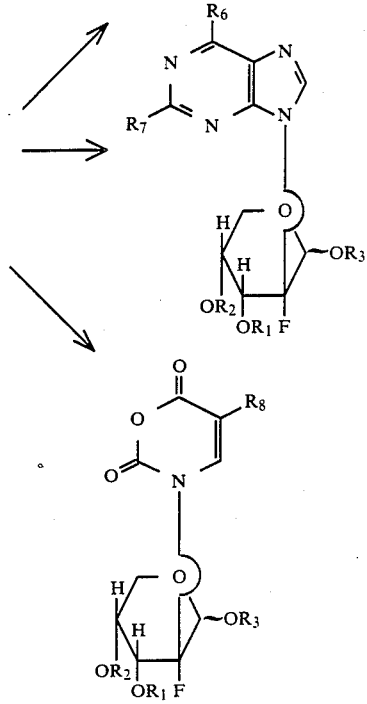

The same hydrolyzable acyl groups described earlier herein can generally be used in the above synthesis of the 2-fluoro 2-deoxyarabinopyranosyl halide. Step (d) of that synthesis can be accomplished by conventional acylation techniques. The step (c) hydrolysis can be performed by contacting an aqueous solution of the compound with a cation exchange resin. Oxidation (step (a)) can be achieved by reaction with conventional oxidizing agents such as nicotinium dichromate. The step (e) halogenation can be effected by contacting the compound with hydrogen bromide or hydrogen chloride, preferably at lower than room temperature, e.g., about 0 to 4 degrees C.

The condensation reaction of the silylated or alkoxylated heterocyclic base with the 2-fluoro-2-deoxyarabinopyranosyl halide can be conducted in a conventional manner for condensing such bases with saccharide halides, for example as disclosed in British patent specification No. 1,070,413. Generally, the reaction is performed by simply mixing the two reactants in an aprotic solvent such as tetrahydrofuran, methylenechloride, 1,2-dichloroethane, benzene, and toluene. Use of a catalyst, such as tin tetrachloride, titanium tetrachloride, and mercury salts, is optional. The precise temperature and duration of the reaction are not critical and may be varied widely depending upon the reactants and solvents employed. However, high temperatures promote decomposition of the saccharide halide and are therefore not preferred. Generally, the reaction temperature can be varied between about 10 degrees and 80 degrees C. for 1 hour to several days or weeks, with the longer times being used at the lower temperatures and with the less reactive heterocyclic bases.

To unblock the 3' and 4' oxygens of the 2'-fluoro-2'-deoxy arabinopyranosyl nucleosides described above requires a conventional saponification treatment, for example using methanolic hydrogen chloride or using an enzyme such as porcine liver esterase (Sigma).

Separation of the α and β anomers of the nucleosides and nucleotides of the present invention can be accomplished using conventional column chromatography and crystallization procedures.

Nucleotides in general are prepared from corresponding nucleosides by direct phosphorylation using $POCl_3$ and trialkyl phosphate(s). This process has been employed to prepare the 5'-phosphates of cytosine arabinoside and 5-fluoro-2'-deoxyuridine in good yields (60-70 percent, pure) from the corresponding nucleosides. Conversion of nucleotides to morpholidates has been achieved in excellent yields, about 95 percent. Synthesis utilizing protecting groups or other phosphorylating reagents can be employed for the preparation of nucleotide components, such as pyrophosphoryl choride/m-cresol or o-chlorophenol; di(2-t-butylphenyl)-phosphorochloridate; cyanoethyl phosphate; 2,2-trichloroethyl-phosphorodichloridate; and dinitrobenzyl phosphorochloridate. The direct phosphorylation method is of sufficiently general utility to effectively yield adequate quantities of 4'-nucleotides, even if separation of other minor (3') isomers is required in some instances. This serves to avoid longer synthetic approches involving protective group chemistry.

The compounds of this invention can be used in oral, injection and perfusion treatment of cancers in substantially the same manner as prior known nucleoside derived compounds.

The compounds of this invention can be used in admixture with pharmaceutically acceptable organic or inorganic carriers suitable for parenteral, external or topical applications, it being understood that carriers suitable for use with the present compounds will not react in a deleterious manner with the compounds. Suitable, pharmaceutically acceptable carriers include, but are not limited to, water, salt solutions, alcohols, vegetable oils, polyethylene glycols, gelatin, lactose, amylose, magnesium stearate, talc, silicic acid, paraffins, perfume oils, fatty acid mono and diglycerides, hydroxy alkylcelluloses, polyvinyl pyrrolidone and the like.

The pharmaceutical preparations may also optionally include auxiliary agents such as lubricants, preservatives, stabilizers, wetting agents, emulsifiers, buffers, salts for influence of osmotic pressure, flavoring, coloring and like substances which are nonreactive with the active compounds.

For parenteral application, particularly useful are oily or aqueous sonicated solutions as well as suspensions and emulsions.

Enteric application can be realized by compounding the compounds as tablets, capsules with carriers and binders of talc, carbohydrate or the like. Sustained release properties may be included by the utilization of differentially degradable coatings such as microencapsulation, multiple coatings or the like.

As topical applications, the compounds are employed in compositions having consistencies ranging from viscous to solid non-sprayable utilizing pharmaceutically acceptable carriers commonly used in topical applications. Suitable formulations include but are not limited to solutions, suspensions, creams, oinments, emulsions, powders, liniments, salves and the like which may include such auxiliary agents as preservatives, stabilizers, wetting agents, buffers and the like.

Sprayable aerosol formulations incorporating the active compounds of this invention are also within the purview of topical application, the active compound preferably in combination with a solid or liquid inert carrier packaged in a suitable dispensing container, pressurized by means of a volatile, normally gaseous propellant, such as freon and the like.

In topical formulations, the active compounds of this invention are utilized at concentrations of from about 5 to about 10 percent by weight.

The novel compounds of the present invention are generally administered to animals, including but not limited to mammals and birds with a cytoxically effective daily dosage of the active compound from about 50 mg/kg animal body weight to about 500 mg/kg animal body weight. This dosage amount will usually be administered in multiple daily dosages.

It is to be appreciated that the actual preferred and effective amounts of the compounds of this invention used will vary according to the specific compound being utilized, the particular compositions formulated, the application mode, as well as the particular sites and organism being subjected to treatment. Factors which generally tend to modify drug action will be taken into consideration by those of skill in the art, such factors as age, weight, sex, diet, times and methods of administration, reaction sensitivities, severity of the condition treated, etc. Optimal application rates for any given set of conditions can be determined by those skilled in the art employing conventional dosage determination tests, considering the foregoing guidelines.

The following specific embodiments are set forth to illustrate the preparation and use of the compounds of the present invention and are not to be construed as limitative. Unless otherwise indicated, all parts and percentages are by weight.

The thin layer of chromatography was performed on EM Science Silica Gel 60F. The column chromatography was carried out with silica gel (230-400 mesh) from E. Merck Industries Co. All melting points were taken on a Mel-Temp capillary point block and are not corrected. The optical rotations were measured on a Perkin-Elmer Polarimeter 241 MC. The nuclear magnetic resonance spectra were determined on a Varian XL100 and Bruker (200 MHz) spectrometers using tetramethylsilane or $CFCL_3$ as internal standards. Mass spectral fragmentation was carried out on Finnigan 4000 GC-MS system 70 (eV) with intermediate resolution Elemental analyses for carbon, hydrogen, nitrogen and fluorine were carried out by Galbraith Laboratories, Inc., Knoxville, TN.

EXAMPLE 1

Preparation of Methyl 3,4-di-0-acetyl-2-deoxy-2(R)-[1H,3H-2,4-dioxo-1-pyrimidinyl]-2-fluoro-α-D-arabinopyranoside [5a] and methyl 3,4-di-0-acetyl-2-deoxy-2(R)-[1H,3H-2,4-dioxo-1-pyrimidinyl]-2-fluoro-β-D-arabinopyranoside [6a]

[Drug No. 85024-Comprising Mixture of Anomers 5a and 6a See FIG. 1]

Step I: Preparation of Methyl 3,4-0-isopropylidine-β-D-erythropentopyranosid-2-ulose (compound 1, $R_3=CH_3$ FIG. 1).

In a round bottomed three-necked flask (5 L) was placed methylene chloride (1.9 L) and pyridine (209.2 mL), and to this was added $CrO_3$ (129.2 g, 1.29 mole) in small fractions for a period of 10 minutes. After completion of $CrO_3$-2 pyridine complex in 15 minutes, a solution of methyl 3,4-0-isopropylidine-β-arabinopyrpanoside (66 g, 0.32 mole) in methylene chloride (500 mL) was added dropwise to the mixture of the oxidizing reagent with magnetic stirring in a period of 30 minutes. Acetic anhydride (122.2 mL, 1.29 mole) was added to this mixture at once and the reaction was completed after stirring at room temperature for 2 hours. After concentration to about 300 mL, the mixture was poured into ethyl acetate (2 L). The slurry mixture was applied to a silica gel column (8×60 cm). The column was further eluted with ethyl acetate. Total effluent (4 L) was collected, evaporated to crystals and dried in vacuo to give 54.7 g (83.7%). The crude mixture was recrystallized from ethyl acetate to give colorless crystals; m.p. 87°–88° C., $[\alpha]_D^{20} = -155.80°$ (c, 0.69, CHCl$_3$) ir (KBr), 1740 (C=O), no OH (no hydrate form [Rosenthal, et al.: Can. J. Chem., 48, 3253 (1970)], $^1$H-n.m.r. (CDCl$_3$+TMS)δ, 4.68 (1,s,H-1) 4.65 (1,d,J$_{3,4}$=5 Hz,H-3), 4.52 (1, dd, J$_{4,3}$=5 Hz, J$_{4,5}$=1.5 Hz, H-4), 4.23 (1, dd, J$_{5,5'}$=12 Hz, J$_{5,4}$=1.5 Hz, H-5*, 4.04 (1, d, J$_{5'5}$=12 Hz, H-5'*), 3.49 (3,s,OCH$_3$), 1.44 and 1.39 (6,2s, isopropyl, $^{13}$C-n.m.r. (CDCl$_3$=TMS)δ, 198.5 (C-2), 110.3 (=CMe$_2$), 100.8 (C-1), 77.6 (C-3), 75.3 (C-4) 58.3 (C-5), 55.6 (OCH$_3$), 27.1 and 26.1 (2 CH$_3$).

*could be interchanged; **could be interchanged

Step II: Preparation of Methyl 2-deoxy-2,2-difluoro-3,4-0-isopropylidene-D-erythropentopyranoside (Compound 2, R$_3$=CH$_3$ FIG. 1).

To an ice-cold solution of methyl 3,4-0-isopropylidene-β-D-erythropentopyranoisid-2-ulose (Rosenthal et al, supra) (45.16 g, 0.22 mole) in dry benzene (400 mL) was added dropwise to a solution of diethylaminosulfurtrifluoride (DAST) [Middleton, W. J.: J. Org. Chem., 40, 574 (1975)] (54 g, 0.33 mole) in dry benzene (100 mL) for a period of 30 minutes, then the reaction mixture was stirred at room temperature for 18 hours. The mixture was diluted with ether (150 mL) and filtered through glasswool. Ice-water (200 mL) was slowly added to the cooled filtrate. The separated organic layer was neutralized with saturated NaHCO$_3$ solution (200 mL×3) with care, washed with water (200 mL×3), and dried over Na$_2$SO$_4$. The organic solvent was removed by evaporation and the residue was distilled at 104°–104.5° C. at 0.2 mmHg to give clear yellowish liquid; yield 38.5 g (78.1%), m/z =209 (M+ −Me).

Step III: Preparation of Methyl 3,4-di-0-acetyl-2-deoxy-2,2-difluoro-D-erythro-pentopyranoside (Compound 3, R$_1$=R$_2$-acetyl, R$_3$=CH$_3$ FIG. 1).

Methyl 2-deoxy-2,2-difluoro-3,4-0-isopropylidene-D-erythro-pentopyranoside (Compound 2) (4 mL, 0.021 mole) was shaken with 15 mL of 95% formic acid at room temperature for 8.5 minutes. The mixture was immediately evaporated to a syrup under reduced pressure below 30° and the residue was dried in vacuo (0.2 mm Hg) for 10 minutes. The residue was evaporated with ethanol (10 mL ×2) and toluene (10 mL×2), and dried in vacuo for 15 minutes. The residual hydrolyzed sugar was treated with pyridine (30 mL) and acetic anhydride (15 mL) at room temperature for 16 hours. After being treated with ice-water (30 mL), the mixture was evaporated to a syrup, coevaporated with tolune (10 mL×3), and dried in vacuo to give a clear yellow syrup which was used for the next step without further purification.

Step IV: Method A

The obtained compound 3 (R$_1$=R$_2$=acetyl, R$_3$=CH$_3$) (0.021 mole) was dissolved in dry methylene chloride (30 mL), cooled with an ice-water bath, and the mixture was bubbled with dry HBr gas for 10 minutes. After it was stirred at 0° for 20 minutes and at room temperature for 15 minutes, the reaction mixture was immediately evaporated under reduced pressure below 30° and dried in vacuo for 20 minutes to give a dark brownish syrup (methyl 3,4-di-0-acetyl-2-deoxy-2-bromo-2-fluoro-D-arabinopyranoside (Compound 4, R$_1$=R$_2$=acetyl, R$_3$=CH$_3$, X=Br). This syrup was used for the next step without further purification.

To an ice-cold solution of trimethylsilylated uracil (0.054 mole) in dry methylene chloride (80 mL) was added dropwise a solution of the freshly prepared compound 4 (R$_1$=R$_2$=acetyl, R$_3$=CH$_3$,X=Br)(0.021 mole) in dry methylene chloride (80 mL) for a period of 20 minutes followed by HgO (4.8 g, 0.022 mole) and HgBr$_2$ (1.6 g 0.0044 mole). [Wittenburg, E.: Chem. Ber., 101, 1095 (1968) and Shimizu, B. et al.: Agr. Biol. Chem., 33, 119 (1969)]. The reaction mixture was stirred at 0° C. for 1 hour and at room temperature for 16 hours. The mixture was diluted with methylene chloride (250 mL) and filtered through a celite (300 G) bed. The filtrate was washed with 15% KI solution. (150 mL ×2), 2% acetic acid (150 mL ×2), water (150 mL ×2), dried over Na$_2$SO$_4$, and filtered. The filtrate was evaporated under reduced pressure below 30° C. to a foamy material. The residue was dissolved in the minimum amount of ethyl acetate/toluene (2:1) mixture and applied to a silica gel column (2.5 ×80 cm) chromatography. The column was eluted with ethyl acetate/toluene (2:1) mixture. The appropriate tubes were pooled and evaporated to a white foamy material; yield 1.7 g (22.5%), Rf=0.31 (silica gel, ethyl acetate/toluene (2:1)), a mixture of α and β isomers in a ratio of about 2:1, 5a and 6a, m/z=360 (M+).

Method B

To an ice-cold solution of the trimethylsilylated uracil (0.027 mole) in dry methylene chloride (20 mL) were added a solution of methyl 3,4-di-0-acetyl-2-deoxy-2,2-difluoro-D-erythro-pentopyranoside (Compound 3, R$_1$=R$_2$=acetyl, R$_3$=CH$_3$) (0.011 mole) in dry methylene chloride (20 mL) and molecular sieves (3A, 8–12 mesh, 3 g) followed by a solution of BF$_3$·Et$_2$O (0.68 mL) [Araki, Y. et al: J. Carbohyd. Chem. 4, 565 (1985)] in methylene chloride (10 mL). The mixture was stirred at 0° C. for 3 hours and at room temperature for 16 hours. A solution of BF$_3$Et$_2$O (0.5 mL) in dry methylene chloride (5 mL) was added to the mixture and the mixture was stirred at room temperature for 16 hours. The mixture was diluted with methylene chloride (150 mL) and filtered through a Celite (300 G) bed. The filtrate was washed with 15% KI solution (75 mL ×2), saturated NaHCO$_3$ solution (100 mL ×2), water (150 mL ×3), dried over Na$_2$SO$_4$, and filtered. The filtrate was evaporated to a foamy material. The residue was applied to a column chromatography in the same way as Method A to give a white foamy solid; yield 456 mg (11.5%) (a mixture of α and β isomers in a ratio of about 2:1). The starting material (compound 3, R$_1$=R$_2$=acetyl, R$_3$=CH$_3$) (750 mg, 25.4%) was recovered.

Separation of α- and β-isomers (5a and 6a) by a silica gel column chromatography.

The mixture of α- and β-isomers (175 mg) was dissolved in the minimum amount of chloroform/isopropanol (20:1) mixture and applied to a dry silica gel column (1.2×70 cm, 230-400 mesh). The column was eluted with chloroform/isopropanol (20:1) mixture. The appropriate tubes (α-isomer, Rf=0.32; β-isomer, Rf -0.39; silica gel; chloroform/isopropanol (20:1) mixture) were collected, evaporated and dried in vacuo to give a foamy solid. α-isomer (60%) β-isomer (30%).

A plurality of known methods have been described in the literature for effecting the separation of anomeric compounds. Under appropriate solvent conditions, the isomers disclosed herein may be purified and separated on a wide variety of chromatographic matrices (i.e. ion exchange chromatography, controlled pore glass chromatography, metal chelate chromatography, dye chromatography, etc.).

The physical data for 5a is as follows:

M.p. 164°-165° C. (dec.), $[\alpha]_D^{20}=88.6°$ (c 0.132, CHCl$_3$), $^1$H-n.m.r. (CDCl$_3$+TMS)δ, 8.75 (1, bs, NH), 7.43 (1, d, J$_{6,5}$=8.17 Hz, H-6 pyrmidine) 5.77 (1, d, J$_{1,F}$=9.8 Hz, H-1), 5.76 (1, dd, J$_{5,6}$=8.17 Hz, $^5$J$_{5,F}$=2.13 Hz, H-5 pyrimidine), 5.49 (1, m, H-4), 5.37 (1, dd, J$_{3,F}$=19.25 Hz, J$_{3,4}$=5.45 Hz, H-3), 4.36 (1, dd, J$_{5,5'}$=10.59 Hz, J$_{5,4}$=5.45 Hz, H-5), 4.22 (1, dd, J$_{5',5}$=10.59 Hz J$_{5',4}$=1.64 Hz, H-5'), 3.41 (3, s, OCH$_3$) 2.12 and 2.11 (6, 2s, 20Ac). Ele. anal. for C$_{14}$H$_{17}$FN$_2$O$_8$ ¼ isopropanol (M. W. 375.32); Calcd. C 47.20%, H 5.10%, N 7.46%, F 5.06%; Found, C 47.54%, H 5.44%, N 7.61%, F 4.74%.

The physical data for 6a is as follows:

$[\alpha]_D^{20}=-93.3°$(c 0.045, CHCl$_3$), $^1$H-n.m.r. (CDCl$_3$+TMS) δ, 8.51 (1, bs, NH), 7.55 (1, d, J$_{6,5}$=8.20 Hz, H-6 pyrimidine), 5.82 (1, d, J$_{1,F}$=2.98 Hz, H-1), 5.76 (1, dd, J$_{5,6}$=8.20 Hz, J$_{5,F}$=2.15 Hz, H-5 primidine), 5.49 (1, m, H-4), 5.43 (1, dd, J$_{3,F}$=17.19 Hz, J$_{3,4}$=6.13 Hz, H-3), 4.39 (1, dd, J$_{5,5'}$=10.64 Hz, J$_{5,4}$=4.83 Hz, H-5), 4.26 (1, dd, J$_{5',5}$=10.64 Hz, J$_{5',4}$=1.55 Hz, H-5'), 3.45 (3, s, OCH$_3$), 2.14 and 2.11 (6, 2s, 20Ac).

EXAMPLE 2

Preparation of Methyl 3,4-di-0-acetyl-2-deoxy-2(R)-[1H,3H-2,4-dioxo-5-fluoro-1-pyrimidinyl]-2-fluoro-α-D-arabinopyranoside [5b] and Methyl 3,4-di-0-acetyl-2-deoxy-2(R)-[1H,3H-2,4-dioxo-5-fluoro-1-pyrimidinyl]-2-fluoro-β-D-arabinopyranoside[6b]

[Drug No. 85027-Comprising Mixture of Anomers 5b and 6b-see FIG. 1]

Drug No. 85027 was prepared substantially in accordance with the method described in Example 1, however, 5-fluorouracil was used as a starting material instead of uracil.

The physical data for 5b is as follows:

M.p. 188°-189° C. (dec.) $[\alpha]_D^{20}=+129.0°$ (c 0.1, CHCl$_3$), $^1$H-n.m.r. (CDCl$_3$+TMS)δ, 9.59 (1, bs, NH), 7.52 (1, d, J$_{6,5}$=5.87 Hz, H-6 pyrimidine), 5.75 (1, d, J$_{1,F}$=7.53 Hz, H-1), 5.48 (1, m, H-4), 5.40 (1, dd, J$_{3,F}$=19.50 Hz, J$_{3,4}$=6.08 Hz, H-3), 4.36 (1, dd, J$_{5,5'}$=10.70 Hz, J$_{5,4}$=5.56 Hz, H-5), 4.23 (1, d, J$_{5',5}$=10.70Hz, H-5'), 3.45 (3, s, OCH$_3$), 2.17 and 2.10 (6, 2s, 20Ac). Ele. anal. for C$_{14}$H$_{16}$F$_2$N$_2$O$_8$ ½H$_2$O(M.W. 387.29); Calcd., C 43.42%, H 4.42%, N 7.23%, F 9.81%; Found, C 43.78%, H 4.44%, N 6.98%, F 9.54%.

The physical data for 6b is as follows:

$[\alpha]_D^{20}=-32.10°$ (c 0.1, CHCl$_3$), $^1$H-n.m.r. (CDCl$_3$+TMS)δ, 9.52 (1, bs, NH), 7.62 (1, d, J$_{6,5}$=6.04 Hz, H-6 pyrimidine), 5.81 (1, s, H-1), 5.43 (2, m. H-3 and H-4), 4.40 (1, dd, J$_{5,5'}$=10.67 Hz J$_{5,4}$=6.08 Hz, H-5), 4.27 (1, d, J$_{5',5}$=10.67 Hz, H-5'), 3.47 (3, s, OCH$_3$), 2.15 and 2.11 (6, 2s, 20Ac).

EXAMPLE 3

Preparation of Methyl 3,4-di-0-acetyl-2-deoxy-2(R)-[1H,3H-2,4-dioxo-5-methyl-1-pyrimidinyl]-2-fluoro-α-D-arabinopyranoside [5c] and Methyl 3,4-di-0-acetyl-2-deoxy-2(R)-[1H,3H-2,4-dioxo-5-methyl-1-pyrimidinyl]-2-fluoro-β-D-arabinopyranoside [6c]

[Drug No. 85060-Comprising a Mixture of Anomers 5c and 6c- see FIG. 1]

Drug No. 85060 was prepared substantially in accordance with the method described in Example 1, however, 5-methyluracil was used as a starting material instead of uracil.

The physical data for 5c is as follows:

M.p. 203°-205° C.(dec.), $[\alpha]_D^{20}=+50.0°$ (c 0.15, CHCl$_3$), $^1$H-n.m.r. (CDCl$_3$+TMS)δ, 8.54 (1, 6s, NH), 7.26 (1, s, H-6 pyrimidine), 5.75 (1, d, J$_{1,F}$=10.72 Hz, H-1), 5.49 (1, m, H-4), 5.38 (1, dd, J$_{3,F}$=19.11 Hz, J$_{3,4}$=6.13 Hz, H-3) 4.36 (1, dd, J$_{5,5'}$=10.80 Hz, J$_{5,4}$=4.78 Hz, H-5), 4.21 (1, dd, J$_{5',5}$=10.80 Hz, J$_{5',4}$=1.07 Hz, H-5'), 3.40 (3, s, OCH$_3$), 2.12 and 2.11 (6, 2s, 20Ac), 1.92 (3, s, CH$_3$ thymine). Ele. Anal. for C$_{15}$H$_{19}$FN$_2$O$_8$(M. W. 374.33); Calcd, C 48.13%, H 5.12%, N 7.49%, F 5.08%; Found, C 47.96%, H 5.50%, N 7.21%, F 5.02%

The physical data for 6c is as follows:

$[\alpha]_D^{20}=+43.6°$ (c 0.05, CHCl$_3$), $^1$H-n.m.r. (CDCl$_3$+TMS)δ, 8.86 (1, bs, NH), 7.36 (1, s, H-6 pyrimidine), 5.82 (1, d, J$_{1,F}$=4.8 Hz, H-1) 5.49 (1, m, H-4), 5.39 (1, dd, J$_{3,F}$=19.21 Hz, J$_{3,4}$=6.04 Hz, H-3), 4.41 (1, dd, J$_{5,5'}$=9.86 Hz, J$_{5,4}$=6.23 Hz, H-5), 4.32 (1, d, J$_{5',5}$=9.86 Hz, H-5'), 3.44 (3, s, OCH$_3$), 2.12 and 2.11 (6H, 2s, 20Ac), 1.94 (3, s, CH$_3$ thymine).

EXAMPLE 4

Preparation of Methyl 2-deoxy-2(R)-[1H,3H-2,4-dioxo-1-pyrimidinyl]-2-fluoro-3,4-di-0-hexanoyl-α-D-arabinopyranoside [5d] and Methyl 2-deoxy-2(R)-[1H,3H-2,4-dioxo-1-pyrimidinyl]-2-fluoro-3,4-di-0-hexanoyl-β-D-arabinopyranoside [6d]

[Drug No. 85058-Comprising a Mixture of Anomers 5d and 6d-See FIG. 1]

To an ice-cold solution of methyl 2(S)-2-bromo-2-fluoro-3,4-di-0-hexanoyl-D-arabinopyranoside (0.009 mole) in methylenechloride (80 mL) (prepared by a similar method to compound 4(R$_1$=R$_2$=acetyl, R$_3$=CH$_3$,X=Br) except using hexanoyl chloride instead of acetic anhydride for the acylation) was added dropwise a solution of trimethylsilylated uracil (0.054 mole) in methylenechloride (80 mL) followed by HgO (4.8 g) and HgBr$_2$ (1.6 g). The mixture was stirred at 0° C. for 2 hours and at room temperature for 16 hours. The mixture was prepared according to Method A. The residue was purified by a silica gel column chromatography (230-400 mesh, 2.5×75 cm). The column was eluted with ethyl acetate/toluene (1:1) mixture. The appropriate tubes were pooled, evaporated to a syrup and dried in vacuo; yield 1.23 g (29.0%), mixture of α/β-isomers (2:1) ratio, Rf=0.53 (silica gel, ethyl acetate/toluene (2:1) mixture), M/Z =472 (M+). Ele. Anal. for $C_{22}H_{33}FN_2O_8$ ½ ethyl acetate (M.W. 516.56): Calcd, C 55.80%, H 7.22%, N 5.42%, F 3.68%; Found, C 55.95%, H 7.17%, N 5.31%, F 3.49%.

EXAMPLE 5

Preparation of Methyl 3,4-di-0-acetyl-2-deoxy-2(R)-[4-acetylamino-2-oxo-1,2-dihydro-1-pyrimidinyl]-2-fluoro-α-D-arabinopyranoside [5e] and Methyl 3,4-di-0-acetyl-2-deoxy-2(R)-[4-acetylamino-2-oxo-1,2-dihydro-1-pyrimidinyl]-2-fluoro-β-D-arabinopyranoside [6e]

[Drug No. 86014-(cytosine derivative) Comprising a Mixture of Anomers 5e and 6e-See FIG. 1]

To an ice-cold solution of compound $4(R_1=R_2=$acetyl, $R_3=CH_3, X=Br)$(0,009 mole) in methylene-chloride (80 mL) was added dropwise a solution of trimethylsilylated $N^4$-acetylcytosine (0.033 mole) in methylenechloride (80 mL) for a period of 30 minutes followed by HgO (5.0 g), HgBr$_2$(1.6 g) and molecular sieves (3A, 5.0 g). The reaction mixture was worked up according to a similar procedure as recited in Method A. The residue was applied to a column chromatography (230-400 mesh, 2.5 ×90 cm). The column was eluted with ethyl acetate/isopropanol (7:1) mixture. The appropriate tubes were pooled and evaporated to a foamy material; yield 0.685 g (19.0%), mixture of α/β-isomers (64:36 ratio), m.p. 189°-190° C. (dec.) $^{19}$F-nmr chemical shift −127.1 (δ) for α-isomer, −123.8 (α) for β-isomer from CFCl$_3$, M/Z=401 (M+).

EXAMPLE 6

Preparation of Methyl 3,4-di-0-acetyl-2-deoxy-2(R)-[4-amino-2-oxo-1,2-dihydro-1-pyrimidinyl]-2-fluoro-α-D-arabinopyranoside [5f] and Methyl 3,4-di-0-acetyl-2-deoxy-2(R)-[4-amino-2-oxo-1,2-dihydro-1-pyrimidinyl]-2-fluoro-β-D-arabinopyranoside [6f]

[Drug No. 86023 Comprising a Mixture of Anomers 5f and 6f-See FIG. 1]

To an ice-cold solution of 15 mL of 0.1 M ZnBr$_2$ [Kierzek, R. et al.: Tetrahed. Lett., 22, 3761(1981)] in methanol/chloroform (4:1) mixture was added 30 mg of methyl 3,4-di-0-acetyl-2-deoxy-2(R)-[4-acetylamino-2-oxo-1,2-dihydro-1-pyrimidinyl]-2-fluoro-D-arabinopyranoside [5e and 6e] and then the mixture was stirred at 0° for 10 minutes. The mixture was immediately evaporated to dryness under reduced pressure below 30° C. and the residue was dissolved in ethyl acetate (10 mL). The ethyl acetate solution was washed with cold water (2 mL ×4), dried over Na$_2$SO$_4$, filtered, evaporated and dried in vacuo to give pale yellowish solid. Rf=0.45 for the starting material 5e and 6e and Rf=0.13 for the product 5f and 6f (silica gel, ethyl acetate/isopropanol (4:1) mixture). The residue was applied to a preparatory thin layer chromatography (tlc) (Silica Gel 60F-254, 10×20 cm, 0.25 mm, EM reagent, ethyl acetate/isopropanol (4:1) mixture). The appropriate band was scraped out and extracted with acetone (10 mL ×3). The acetone suspension was filtered through an ultra-fine fritted disc filter (maximum pore size 0.9-1.4 m). The filtrate was evaporated, coevaporated with toluene (5 mL ×3), and dried in vacuo to give white powdery solid; yield 9.5 mg (35.3%), m.p. 195°-196° C. (dec.).

EXAMPLE 7

Preparation of Methyl 2-deoxy-3,4-0-isopropylidene-2-rac-[1H,3H-2,4-dioxo-1-pyrimidinyl]-2-fluoro-α-D-arabinopyranoside [5g] and Methyl 2-deoxy-3,4-0-isopropylidene-2-rac-[1H,3H-2,4-dioxo-1-pyrimidinyl]-2-fluoro-β-D-arabinopyranoside [6g]

[Drug No. 85023 Comprising a Mixture of Anomers 5g and 6g-See FIG. 1]

To an ice-cold mixture of compound 4($R_1$, $R_2$=isopropylidene, $R_3=CH_3, X=Cl$ 0.0045 mole) [prepared from compound 3 ($R_1,R_2$=isopropylidene,$R_3=CH_3$) a method similar to that used to prepare compound 4] and trimethylsilylated uracil (0.009 mole) was added dropwise a solution of SnCl$_4$(0.52 mL) in 1,2-dichloroethane (10 mL) for a period of 30 minutes. The mixture was continuously stirred at 0° for 1.5 hours and then at room temperature for 16 hours. The reaction mixture was diluted with 1,2-dichloroethane (150 mL) and filtered through a Celite (300 G) bed. The filtrate was washed with 15% KI solution (150 ml ×2), sat. NaHCO$_3$ solution (150 mL ×2), water (150 mL ×3), dried over Na$_2$SO$_4$, and filtered. The filtrate was evaporated under reduced pressure below 30° to a foamy material. The residue was chromatographed on a column of silica gel (230-400 mesh, 1.5×80 cm). The column was eluted with ethyl acetate/toluene (2:1) mixture. The appropriate white foamy material; yield 0.332 g (23.3%), m.p. 187°-188° (dec.), Rf=0.32 (silica gel, ethyl acetate/toluene (2:1) mixture). The configuration of the glyosidic linkage (2') is not certain. M/Z=316 (M+).

EXAMPLE 8

The results of antitumor evaluations carried out are presented in Tables 1-5. The results indicate that the compounds in accord with the present invention have produced a significant increase in life span of L1210 tumor bearing mice.

In conducting the evaluations, the activity was tested against intraperitoneal (i.p.) implanted leukemia in mice. In conducting the tests the ascites form of L1210 lymphoid leukemia (E. Law et al., J. Nat. Cancer Inst. 10:179-192, 1949) grown in DBA/2N mice, were employed. The assay was performed similarly to the National Cancer Institute (NCI) protocol 3LE31, described in In Vivo Cancer Models, NIH Publication 84-2635, Feb. 1984, the disclosure of which is hereby incorporated by reference.

DBA/2N female mice (20 g) were implanted i.p. with $1\times10^6$ L1210 leukemia cells on day 0. Mice were weighed and inspected for tumor growth and survival daily. Drug (85024) was dissolved in 0.5% Tween 80 in saline (0.2 ml) and injected i.p. daily on days 1 through 5. Dosages varied from 1 to 800 mg/kg/day (mkd).

The control group consisted of 20 mice injected with a 0.2 ml suspension of 0.5% Tween 80 in saline.

Survival time was measured in days after tumor implantation. % ILS (increase in life span) was based on mean survival. Statistical significance is based on the Cox-Mantel (Cox, D. R., J. Royal Stat. Soc., Series B 34

: 187–220, 1972) or Dunn test (Dunn, O. J., Technometrics, 6 : 241–252, 1964).

Testing was followed as described in the NCI protocol and evaluation by comparison of median survival time (ST) of the treated animals to that of the control animals by the percentage increase in % ILS.

Table 2 summarizes the results obtained against L 1210/0 by i. p. treatments with a mixture of α and β anomers in a ratio of about 2:1 the compound 85024.

Maximal therapeutic efficacy using a 5 day i. p. injection schedule (1 dose per day on days 1 through 5) was achieved at 500 mg/kg/day ×5. Dosages above 500 mkd resulted with increased host toxicity as evidenced by increased weight loss and eventual mortality due to drug toxicity at 800 mkd (Table 2).

EXAMPLE 9

Compounds 85024, 85023, 85058, 85027 and 85060 having a glycosidic linkage between the 2'carbon of the arabinose (in pyranose configuration) and base were evaluated for their growth inhibitory action on L1210 leukemia cells maintained in RPMI 1640 medium supplemented with 10% fetal calf serum and 16 mM HEPES, pH 7.2. Cellular growth inhibition was determined by incubating $5 \times 10^{-4}$ cells/ml for 48 hr in 2 ml of media containing varying concentrations of drugs. Cell growth inhibition (50% growth inhibitory concentration, $IC_{50}$) was determined after counting cells with a Coulter counter (Bernacki et al., Cancer Res. 45, 695, 1985). Drug concentrations which inhibited cell growth by 50% ($IC_{50}$) are listed for each compound in Table 1.

Drug 85024 (a mixture of the α and β anomers in a ratio of about 2:1, 5a and 6a in FIG. 1) inhibited 50% of cell growth at $5.5 \times 10^{-5}$ M. Blocking the 3'and 4'carbons with an isopropylidene group (85023) resulted with a loss in biological inactivity. Substituting hexanoyl (85058) for the acetyl groups did not significantly affect activity. The 5-fluoro analog (85027) demonstrated similar biological activity as compared with 85024, while the thymine derivation (85060) was inactive.

EXAMPLE 10

The therapeutic activity of 85027 was compared with that of 5-Fluorouracil (5-FU) and Cytosine Arabinoside (ara-C) in DBA/2 mice with L1210 Leukemia. (Table 3) Tests were performed in accordance with the procedure described in Example 8. Eight mice were used as controls and five mice for each drug dosage group. Drugs were administered i.p. once per day on days 1, 2, 3, 4 and 5 except where noted otherwise. 5-FU was administered i.p. on days 1,3 and 6.

By comparison 85027 demonstrated less therapeutic activity than araC at 200 mkd×5. 5-FU at dosages of 50, 100 and 200 mkd×5 were extremely toxic to mice causing severe weight loss (to 13–14 g). Dosages of 5 or 25 mkd×3, administered on days 1, 3 and 6, were more effective increasing the life span of leukemic mice to 41 and 88%, respectively. Ara-C administered i.p. on a 5 day schedule at 50, 100 and 200 mg/kg was most effective causing a doubling of lifespan.

EXAMPLE 11

The therapeutic activity of 85024 was evaluated in DBA/2N female mice implanted i.p. with either $10^6$ L1210 luekemia cells resistant to ara-C (L1210/ara-C) or 5-FU (L1210/5-FU). Drug resistant L1210 leukemia cell sublines were obtained from the National Cancer Institute. The procedures for drug evaluation were similar to those described in Example 8. Eight mice were used as controls and five mice for each drug dosage group. Drugs were administered i.p. once per day on days 1, 2, 3, 4 and 5.

By comparison, 85024 displayed a significant 57% ILS in DBA/2N mice with L1210-ara-C leukemia while ara-C administration demonstrated no therapeutic effect (Table 4). Similarly, 85024 at dosages of 100 and 200 mkd×5 demonstrated small (22 and 11% ILS) therapeutic effects in mice with L1210/5-FU leukemia while 5-FU (25 mkd×5) did not.

EXAMPLE 12

The therapeutic activity of 85024 was evaluated in C57/B16 female mice implanted s.c. with either Lewis lung carcinoma or M5076 sarcoma (Table 5).

C57/B16 female mice were implanted s.c. using a trochar on day 0 with a 50 mg piece of either Lewis lung carcinoma of M5076 sarcoma. Drugs were administered i.p. once daily on days 3, 4, 5, 6 and 7. Tumor size (two perpendicular diameters) was measured with calipers and volume was estimated algebraically. Survival was monitored daily for 60 days. % ILS (increase in life span) is based on median survival.

Dosages i.p. of 400 mg/kg/day administered once daily for 5 days on day 3, 4, 5, 6 and 7 resulted with a 40% ILS and a statistically significant decrease in tumor size. The median day to reach half maximal tumor size (normalized for animal weight) increased by 4 days, from day 19 to 23. Similarly, 85024 administered identically to mice with M5076 tumor caused a small ILS of 14% and a statistically significant decrease in tumor size; half maximal tumor size shifted from day 32 to 38.

EXAMPLE 13

Reversal studies were conducted as follows: 82024, 85027 or 5-FdUr were added at various concentrations near their $IC_{50}$ to cultures of L1210 leukemia cells, maintained in PRMI 1640 medium supplemented with 10% fetal calf serum and 16mM HEPES, pH 7.2 as described in Example 9. Nucleosides including thymidine ($1 \times 10^{-5}$M), uridine ($1 \times 10^{-4}$M), deoxyuridine ($1 \times 10^5$M), adenosine ($1 \times 10^{-4}$M), or guanosine ($1 \times 10^{-5}$M) were also added to identical drug (85024, 85027 or 5-FdUr) containing L1210 leukemia cultures. Cellular growth inhibition or its prevention by the addition of salvageable nucleosides was determined 48 hours later by counting cells using an electronic Coulter Counter.

5-Fluorodeoxyuridine (5-FdUr) causes L1210 cellular growth inhibition by binding to thymidylate synthetase and limiting de novo thymidine biosynthesis. The addition of exogenous thymidine to L1210 cell cultures reverses this block and prevents 5-FdUr cytotoxicity. The addition of $1 \times 10^{-5}$M thymidine to cultures of L1210 leukemia cells increased the $IC_{50}$ of 5-FdUr from $3 \times 10^{-10}$M to $>1 \times 10^{-8}$M. Thymidine ($1 \times 10^{-5}$M), uridine ($1 \times 10^{-4}$M) or deoxyuridine ($1 \times 10^{-5}$M), only marginally (<10%) affected the $IC_{50}$ of 85024 or 85027 suggesting a different mechanism of action for these agents as compared with 5-FdUr.

Significance of Examples 8–13

Several of the 2' coupled fluorine substituted pyrimidine nucleoside analogs inhibited tumor cell growth in vitro ($10^{-5}$ to $10^{-4}$M range) and increased the life span of mice with L1210, L1210/ara-C and L1210/5-FU leukemia by 20 to 57% (100 to 500 mkd×5). 85024 administration to mice with s.c. solid tumors (Lewis lung carcinoma or M5076 sarcoma) also increased their lifespan and significantly decreased tumor size. 85024 and 85027 cellular cytotoxicity in tissue culture was not reversed by exogenous thymidine, uridine or deoxyuridine indicating a mechanism of action different from 5-FU and 5-FdUr. With the data at hand these agents (85024 or 85027), or other similarly 2' coupled nucleoside analogs, are unique in structure, appear to have a novel cellular mechanism of action which is as yet defined and are not cross resistant to currently available antitumor agents such as aras-C and 5-FU.

From the foregoing description, one skilled in the art to which this invention pertains, can easily ascertain the essential features thereof, and can make various changes and modifications to adapt it to various usages and conditions without departing from the spirit and scope thereof.

TABLE 1

L1210 Leukemia Cell Growth Inhibition by Pyrimidine Nucleoside Analogs

| Drug (CD no.) | $IC_{50}(M)$ |
|---|---|
| 85024 | $5.5 \times 10^{-5}$ |
| 85023 | $>10^{-4}$ |
| 85058 | $4.0 \times 10^{-5}$ |
| 85027 | $3.4 \times 10^{-5}$ M |
| 85060 | $>10^{-4}$ |

TABLE 2

Therapeutic Activity of 85024 Against i.p. Inoculated L1210/0 Leukemic Mice

| Dosage (mkd × 5) | Animals per Group | Mean[a] Animal Weight (g) | Range (days) | Median (days) | Mean ± SD (days) | % ILS | p Values[b] |
|---|---|---|---|---|---|---|---|
| 0 | 20 | 22.5 | 6–8 | 7 | 6.7 ± 0.1 | — | — |
| 50 | 5 | 23.4 | 7–8 | 7 | 7.2 ± 0.2 | 7 | N.S. |
| 100 | 5 | 24.0 | 8–8 | 8 | 8.0 ± 0 | 19 | N.S. |
| 200 | 10 | 22.0 | 8–10 | 9 | 8.8 ± 0.2 | 31 | p < 0.01 |
| 400 | 10 | 18.8 | 9–11 | 10 | 9.9 ± 0.2 | 48 | p < 0.01 |
| 500 | 5 | 17.3 | 10–11 | 10 | 10.4 ± 0.2 | 55 | p < 0.01 |
| 600 | 5 | 16.8 | 7–11 | 10 | 9.4 ± 0.8 | 40 | p < 0.5 |
| 700 | 5 | 16.6 | 4–7 | 7 | 6.0 ± 0.6 | −10 | N.S. |
| 800 | 5 | 19.5 | 2–2 | 2 | 2.0 ± 0 | −70 | — |

[a] Mean weight of mice on the day of death.
[b] p Values determined by the Dunn test. (Dunn, O. J., Technometrics 6:241-252, 1964)

TABLE 3

Therapeutic Activity of 85027, 5-Fluorouracil (5-FU) and Arabinoside (ara-C) in DBA/2 Mice with L1210 Leukemia

| Drug | Dosage (mkd × 5) | Mean Animal Weight (g) | Range (days) | Median (days) | Mean ± SD | % ILS | p Values |
|---|---|---|---|---|---|---|---|
| 85027 | 50 | 23.3 | 8–8 | 8 | 8 ± 0 | 25 | p < 0.01 |
|  | 100 | 23.2 | 7–8 | 8 | 7.8 ± 0.2 | 22 | p < 0.05 |
|  | 200 | 21.7 | 8–9 | 8 | 8.2 ± 0.22 | 29 | p < 0.01 |
| 5-FU | 5 | 22 | 9–9 | 9 | 9 | 41 | p < .01 |
|  | 25 | 22.8 | 12–12 | 12 | 12 | 88 | p < .01 |
|  | 50 | 13.9 | 8–9 | 9 | 8.6 ± 0.2 | 34 | p < .01 |
|  | 100 | 13.8 | 7–8 | 8 | 7.8 ± 0.2 | 22 | p < .05 |
|  | 200 | 13.3 | 7–8 | 8 | 7.8 ± 0.2 | 22 | p < .05 |
| ara-C | 50 | 20.3 | 9–14 | 14 | 13.0 ± 1.0 | 104 | p < .05 |
|  | 100 | 21.3 | 14–15 | 14 | 14.4 ± 0.2 | 126 | p < .01 |
|  | 200 | 18.3 | 8–19 | 9 | 12.4 ± 2.3 | 95 | p < .01 |
| Control | — | 25.2 | 6–7 | 6 | 6.4 ± 0.2 | — | — |

TABLE 4

Therapeutic Activity of 85024 in DBA/2N Mice with Ara-C or Drug Resistant L1210 Leukemia

| Tumor | Drug | Dosage (mkd × 5) | Animals per Group | Mean[a] Animal Weight (g) | Range (days) | Median (days) | Mean ± SD (days) | % ILS | P Value[a] |
|---|---|---|---|---|---|---|---|---|---|
| L1210/ara-C | — | — | 8 | 20.7 | 7–8 | 7 | 7.1 + 0.1 | — | — |
| L1210/ara-C | 85024 | 100 | 5 | 20.7 | 8–9 | 9 | 8.6 ± 0.2 | 28 | NS |
| L1210/ara-C | 85024 | 200 | 5 | 21.0 | 8–9 | 9 | 8.8 ± 0.2 | 28 | <.01 |
| L1210/ara-C | 85024 | 500 | 5 | 18.6 | 10–11 | 11 | 10.8 ± 0.2 | 57 | <.01 |
| L1210/ara-C | ara-C | 100 | 5 | 20.0 | 7–7 | 7 | 0 | 0 | NS |
| L1210/5-FU | — | — | 8 | 19.7 | 8–10 | 9 | 9.25 ± 0.2 | — | — |
| L1210/5-FU | 85024 | 100 | 5 | 20.6 | 9–12 | 11 | 10.6 ± .5 | 22 | <.05 |
| L1210/5-FU | 85024 | 200 | 5 | 20.2 | 9–11 | 10 | 10 ± 0.4 | 11 | 0.1 |
| L1210/5-FU | 85024 | 500 | 5 | 15.9 | 6–7 | 6 | 6.4 ± 0.2 | −34 | — |
| L1210/5-FU | 5-FU | 25 | 5 | 17.6 | 5–9 | 8 | 7.6 ± 0.7 | 12 | — |

[a] Determined by the Cox-Mantel test. (Cox, D. R., J. Royal Stat. Soc., Series B 34: 187-220, 1972).

TABLE 5

Therapeutic Activity of 85024 in C57/B16 Mice with Solid Tumor

| Tumor | Dosage (mkd × 5) | Survival Parameters | | | | Half Maximal Tumor Volume (day) |
|---|---|---|---|---|---|---|
| | | Animals per grp | Range (days) | Median (days) | % ILS | |
| Lewis lung | 0 | 8 | 21–30 | 22 | — | 19 |
| carcinoma | 50 | 5 | 24–31 | 27 | 22 | 20.5[b] |
| (s.c.) | 200 | 5 | 17–32 | 31 | 40 | 21 |
| | 400 | 5 | 21–31 | 31 | 40[b] | 23[b] |
| M5076 | 0 | 7 | 27–45 | 37 | — | 32 |
| sarcoma | 50 | 5 | 34–60[a] | 36 | 0 | 35[b] |
| | 200 | 5 | 36–42 | 37 | 0 | 35 |
| | 400 | 5 | 33–47 | 42 | 14 | 38[b] |

[a] One animal survived for 60 days but bore a large, frank tumor.
[b] p < 0.05 by the Dunn or Cox-Mantel test.

We claim:
1. A compound having the formula:

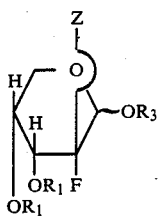

wherein Z is pyrimidinyl-1, purinyl-9, or 1,3-oxazinyl-3, each of $R_1$ and $R_2$ is selected from the group consisting of hydrogen, isopropylidene, $C_{2-12}$ alkanoyl, benzoyl, phenylacetyl, phenylpropionyl, o-, m-, and p-methylbenzoyl, β-cyclopentylpropionyl, and dihydrocinnamoyl, and $R_3$ is hydrogen, methyl, benzyl or a $C_{2-12}$ alkyl group and pharmaceutically acceptable salts thereof.

2. The compound of claim 1 wherein Z is a pyrimidinyl-1 moiety derived from a pyrimidine base having the formula:

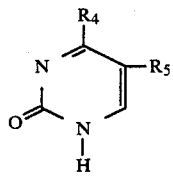

wherein $R_4$ hydrogen is amino, hydroxym nercapto, hydroxylamino, alkylamino, arylamino, or aralkylamino, and $R_5$ is fluoro, bromo, chloro, hydrogen, iodo, mercapto, nitro, nitrilo, thiocyanate, alkyl, alkenyl, or alkynyl.

3. The compound of claim 1 wherein Z is a purinyl-9 moiety derived from a purine base having the formula:

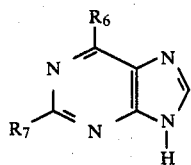

wherein $R_6$ is amino, hydrogen, hydroxylamino, hydroxy, mercapto, chloro, alkylamino, arylamino, or aralkylamino, and $R_7$ is hydrogen, hydroxy, chloro, fluoro, amino, nitro, mercapto, or hydroxyalkyl.

4. The compound of claim 1 wherein Z is a 2,6-dioxo-1,3-oxazinyl-3 moiety derived from an oxazine base of the formula:

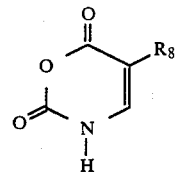

wherein $R_8$ is fluoro, bromo, chloro, hydrogen, iodo, mercapto, nitro, nitrilo, thiocyanate, alkyl, alkenyl, or alkynyl.

5. A compound having the formula:

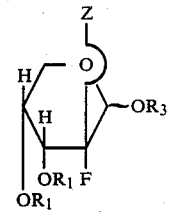

wherein Z is selected from the group consisting of cytosine, uracil, thymine, 5-fluorouracil, 5-azauracil, 5-azacytosine, dihydro-5-azauracil, dihydro-5-azacytosine, 6-azauracil, 6-azacytosine, 3-deazauracil, and 3-deazacytosine, adenine, guanine, 6-chloropurine, hypoxanthine, xanthine, and the 1-deaza, 2-aza, 3-deaza, 7-deaza, 8-aza, 2,8-diaza, 7-deaza-8-aza, and 9-deaza derivatives of said groups, each of $R_1$ and $R_2$ is selected from the group consisting of hydrogen, isopropylidene, $C_{2-12}$ alkanoyl, benzoyl, phenylacetyl, phenylpropionyl, o-, m-, and p-methylbenzoyl, β-cyclopentylpropionyl, and dihydrocinnamoyl, and $R_3$ is hydrogen, methyl, benzyl and a $C_{2-12}$ alkyl group and pharmaceutically acceptable salts thereof.

6. A pharmaceutical composition containing a pharmaceutically effective amount of a compound having the formula:

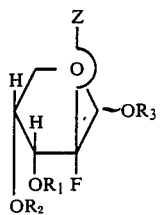

wherein Z is pyrimidinyl-1, purinyl-9, or 1,3-oxazinyl-3, each of $R_1$ and $R_2$ is selected from the group consisting of hydrogen, isopropylidene, $C_{2-12}$ alkanoyl benzoyl, phenylacetyl, phenylpropionyl, o-, m-, and p-methylbenzoyl, β-cyclopentylpropionyl, and dihydrocinnamoyl, and $R_3$ is hydrogen, methyl, benzyl or a $C_{2-12}$ alkyl group and pharmaceutically acceptable salts thereof in combination with a pharmaceutically acceptable carrier.

7. The composition of claim 6 wherein the compound is selected from the group consisting of methyl 3,4-di-O-acetyl-2-deoxy-2(R)-[1H,3H-2,4-dioxo-1-pyrimidinyl]-2-fluoro-β-D-arabino-pyranoside having the formula:

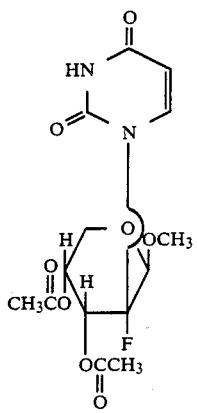

and pharmaceutically acceptable salts thereof.

* * * * *

UNITED STATES PATENT AND TRADEMARK OFFICE
CERTIFICATE OF CORRECTION

PATENT NO. : 4,918,056
DATED : April 17, 1990
INVENTOR(S) : Miroslav V. Bobek et al.

It is certified that error appears in the above-identified patent and that said Letters Patent is hereby corrected as shown below:

Column 1, line 8, after "Cancer Institute" insert --The government may have certain rights in this invention.--.

Column 19, line 20-28    delete the structural formula and substitute --

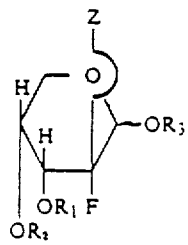

Column 19, line 48,    delete "hydroxym nercapto" and substitute --hydroxy, mercapto--.

UNITED STATES PATENT AND TRADEMARK OFFICE
CERTIFICATE OF CORRECTION

PATENT NO. : 4,918,056
DATED : April 17, 1990
INVENTOR(S) : Miroslav V. Bobek et al.

It is certified that error appears in the above-identified patent and that said Letters Patent is hereby corrected as shown below:

Column 20, line 41-50, delete the structural formula and substitute --

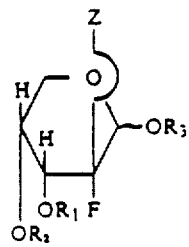

Column 20, at the end of line 55, delete "3-".

Signed and Sealed this

Tenth Day of September, 1991

Attest:

HARRY F. MANBECK, JR.

Attesting Officer

Commissioner of Patents and Trademarks